(12) United States Patent
Kiridena

(10) Patent No.: US 10,073,067 B1
(45) Date of Patent: Sep. 11, 2018

(54) ANALYTICAL METHODS FOR DETERMINING QUALITY OF DIOCTYLTIN BISOCTYLMALEATE

(71) Applicant: Firestone Polymers, LLC, Akron, OH (US)

(72) Inventor: Waruna C. B. Kiridena, Copley, OH (US)

(73) Assignee: Firestone Polymers, LLC, Akron, OH (US)

( * ) Notice: Subject to any disclaimer, the term of this patent is extended or adjusted under 35 U.S.C. 154(b) by 527 days.

(21) Appl. No.: 14/722,332

(22) Filed: May 27, 2015

Related U.S. Application Data

(60) Provisional application No. 62/005,349, filed on May 30, 2014.

(51) Int. Cl.
    *G01N 30/06* (2006.01)
    *C07F 7/22* (2006.01)
    *G01N 30/02* (2006.01)

(52) U.S. Cl.
    CPC ........... *G01N 30/06* (2013.01); *C07F 7/2244* (2013.01); *G01N 2030/027* (2013.01)

(58) Field of Classification Search
None
See application file for complete search history.

(56) References Cited

U.S. PATENT DOCUMENTS 3,433,763 A * 3/1969 Seki ............... C07F 7/2244
    524/178
2009/0043046 A1 2/2009 Luo et al.

FOREIGN PATENT DOCUMENTS

DE     254385 A1 * 2/1988
GB     975369 A * 11/1964 ............... C07F 7/22

* cited by examiner

*Primary Examiner* — Christopher Adam Hixson
*Assistant Examiner* — Michelle Adams
(74) *Attorney, Agent, or Firm* — Meredith E. Hooker; J. Gregory Chrisman

(57) ABSTRACT

Methods are described for determining the quality of dioctyltin bisoctylmaleate and selectively screening its use as a component or modifying agent in a polymer production process. The quality of dioctyltin bisoctylmaleate is determined by measuring the presence and intensity of by products or impurities contained in the dioctyltin bisoctylmaleate. The detected impurities are resolved by comparison to a baseline, such as a solubility limit, to make a decision if the dioctyltin bisoctylmaleate supply is within acceptable limits. Selectively using certain supplies of dioctyltin bisoctylmaleate having suitable limits of impurities, such as the solubility limit of dioctyltin maleate, polymer production efficiency, time and costs can be improved.

16 Claims, 7 Drawing Sheets

ANALYTICAL METHODS FOR DETERMINING QUALITY OF DIOCTYLTIN BISOCTYLMALEATE

This application claims the benefit of U.S. provisional application Ser. No. 62/005,349 filed May 30, 2014, the contents of which are incorporated herein in their entirety by reference.

TECHNICAL FIELD

The present invention relates to methods for determining the quality of dioctyltin bisoctylmaleate by testing a sample, and more particularly, using a HPLC method to analyze the sample to determine the intensity or presence of undesirable components that can affect polymer production.

BACKGROUND

Modifying agents are used in polymer production to react (or modify) an active terminal of an unmodified polymer. The agents can be used to terminate a polymerization reaction and thus can be also referred to as terminating agents. An example of a terminating agent used in polymer production is dioctyltin bisoctylmaleate. Dioctyltin bisoctylmaleate is supplied by various companies, and as such, the purity and quality of dioctyltin bisoctylmaleate supplies can vary from supplier to supplier and from batch to batch. The undesirable components or impurities present in dioctyltin bisoctylmaleate can negatively affect polymer production and efficiency. For example, low quality dioctyltin bisoctylmaleate can result in the formation of precipitates during manufacturing that can clog processing equipment and increase polymer processing time and costs. Further, the precipitates, when present, can be undesirably added to polymer reactions and potentially increase impurities or create by products in the final polymer product.

Presence of undesirable components in dioctyltin bisoctylmaleate, such as impurities or by products, can be confirmed by nuclear magnetic resonance (NMR). Although this useful technique can provide a quantitative analysis of dioctyltin bisoctylmaleate, such as in the research and development area, the technique is not as useful for manufacturing quality control (QC) because QC labs are often not equipped with personnel and/or equipment needed to perform NMR analysis. NMR testing requires expensive equipment and can be time consuming. Thus, NMR is not conducive to time-sensitive polymer production operations. There is, however, a need for efficient QC analysis of dioctyltin bisoctylmaleate supplies to determine quality and purity and that has a high degree of quantitative precision and reproducibility. Such methods of QC analysis can improve the quality of the polymers being produced and reduce costs and delays in polymer manufacturing.

SUMMARY

Provided herein is a process for preparing a polymer and polymers prepared by that process. The process includes sampling a dioctyltin bisoctylmaleate supply to determine its suitability for use as a component in the process for preparing a polymer. The dioctyltin bisoctylmaleate supply is suitable for use when the by product, dioctyltin maleate, is present below its solubility limit in dioctyltin bisoctylmaleate. The dioctyltin bisoctylmaleate sample is analyzed to determine the presence of dioctyltin maleate to thereby evaluate the quality of the dioctyltin bisoctylmaleate supply. The detected presence of dioctyltin maleate is compared to the solubility limit. The solubility limit is selected from at least one of the following: (1) a ratio of relative intensities of dioctyltin bisoctylmaleate and dioctyltin maleate in the sample and/or (2) weight percent of the dioctyltin maleate present in the dioctyltin bisoctylmaleate supply. Based on the analysis and comparison to the solubility limit, a decision is made about the suitability of the dioctyltin bisoctylmaleate supply for use in the process for preparing a polymer.

In one embodiment, the dioctyltin bisoctylmaleate sample is analyzed by high performance liquid chromatography (HPLC), wherein the dioctyltin bisoctylmaleate sample is used to prepare a HPLC test sample.

In one embodiment, the HPLC test sample can include a first solvent and a second solvent or a co-solvent system, wherein the dioctyltin maleate present in the dioctyltin bisoctylmaleate sample is soluble in one or both solvents.

In another embodiment, the first and second solvents in the HPLC test sample are organic and non-aqueous, for example, the first and second solvents can be chloroform and cyclohexane.

In another embodiment, the solubility limit of dioctyltin maleate in dioctyltin bisoctylmaleate can be in the range of 1.8 to 3.2 or above 1.8, wherein the solubility limit is a ratio of the relative intensity of dioctyltin bisoctylmaleate to the relative intensity of dioctyltin maleate. Alternatively, the solubility limit can be in the range of 0.3 to 0.54 or below 0.54, wherein the solubility limit is a ratio of the relative intensity of dioctyltin maleate to the relative intensity of dioctyltin bisoctylmaleate.

In one aspect, the presence of dioctyltin maleate is below or above its solubility limit, for example, depending on the ratio calculated, and a decision is made whether to accept or reject the dioctyltin bisoctylmaleate supply for use in the process for preparing a polymer.

In another embodiment, the solubility limit can be less than 10, 11 or 12 weight percent of dioctyltin maleate that is present in the dioctyltin bisoctylmaleate supply.

In another aspect, the process can include a polymer or product prepared by using the dioctyltin bisoctylmaleate supply or a portion thereof, wherein the supply was accepted for use in the process after determining its quality, such as determining its solubility limit, as described above.

In another embodiment, a HPLC method of evaluating dioctyltin bisoctylmaleate is provided. The method includes preparing a HPLC test sample using a portion of the dioctyltin bisoctylmaleate material. The test sample can include two or more liquids other than the dioctyltin bisoctylmaleate material portion, wherein the dioctyltin bisoctylmaleate material contains dioctyltin maleate and the dioctyltin maleate is soluble in at least one of the two or more liquids of the HPLC test sample. The test sample is analyzed by HPLC to determine at least one of the following: (1) the weight percent of dioctyltin maleate present in the dioctyltin bisoctylmaleate material and/or (2) the relative intensities of dioctyltin maleate and dioctyltin bisoctylmaleate in the sample. The detected presence of dioctyltin maleate, whether its weight percent or ratio of relative intensity to dioctyltin bisoctylmaleate, is compared to its solubility limit in dioctyltin bisoctylmaleate. The solubility limit is selected from at least one of the following: (1) a ratio of relative intensities of dioctyltin bisoctylmaleate and dioctyltin maleate and/or (2) weight percent of the dioctyltin maleate present in the dioctyltin bisoctylmaleate supply. Based on the comparison, it is determined whether the dioctyltin maleate is present in the dioctyltin bisoctylmaleate material below or above its solubility limit to thereby decide whether the dioctyltin bisoctylmaleate is suitable for use as a component of a polymer process.

In one embodiment, the HPLC includes a mobile phase containing the two or more liquids used in the HPLC test sample, the two or more liquids being a first solvent and a second solvent for the dioctyltin maleate.

In another embodiment, the mobile phase can be non-aqueous.

In another embodiment, the relative concentrations of the first solvent and the second solvent being varied to a predetermined gradient. The first and second solvents can be chloroform and cyclohexane.

DETAILED DESCRIPTION

Figure 1:
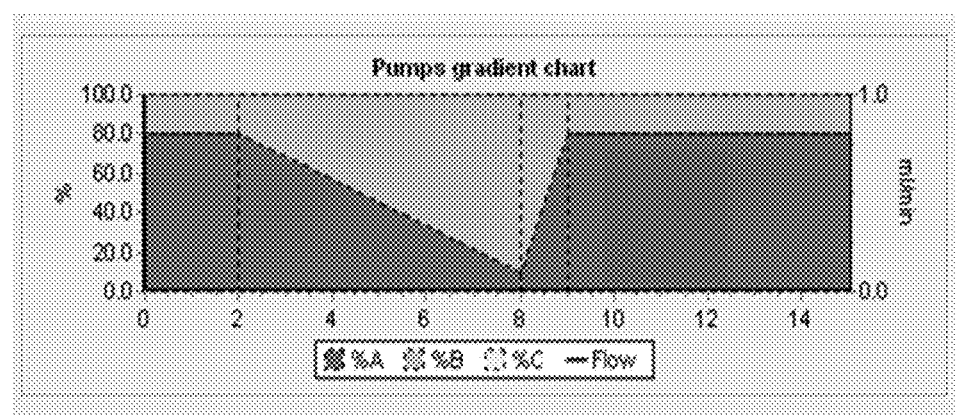
FIG. 1 is a pump gradient chart for a HPLC run using two liquids to evaluate a sample from a dioctyltin bisoctylmaleate supply.

Herein, when a range such as 5-25 (or 5 to 25) is given, this means preferably at least or more than 5 and, separately and independently, preferably not more than or less than 25. In an example, such a range defines independently at least 5, and separately and independently, not more than 25.

Dioctyltin bisoctylmaleate is supplied as a viscous liquid and can contain dioctyltin maleate, which can be a by-product or impurity formed during dioctyltin bisoctylmaleate manufacturing processes. Dioctyltin maleate has the following structure.

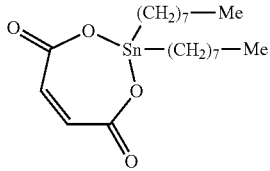

For polymer processes, it is desirable that the dioctyltin bisoctylmaleate is of a certain quality and does not contain solid precipitate, e.g., dioctyltin maleate. The methods described herein are useful from a process standpoint to monitor dioctyltin bisoctylmaleate supplies and ensure batch to batch consistency and quality and to troubleshoot processing problems associated with such potential precipitates or other impurities. An undesirable amount of by products or impurities can cause manufacturing delays, increase costs for producing polymers and result in polymer having additional impurities or by products.

Herein, the term "solubility limit" refers to the maximum presence or solubility of dioctyltin maleate in a dioctyltin bisoctylmaleate supply without the dioctyltin maleate or a portion thereof precipitating as a solid material in the dioctyltin bisoctylmaleate. The solubility limit can be affected by conditions such as temperature. As used herein, the solubility limit is referenced at standard temperature and pressure conditions as known in the art.

The solubility limit of dioctyltin maleate can be used as a reference value. The solubility limit can be a value for the presence of dioctyltin maleate in a sample, for example, a reference sample. The reference value can be numerical and represent aspects of the presence of dioctyltin maleate. For instance, the solubility limit can be characterized as the measured weight percent of the dioctyltin maleate present in the dioctyltin bisoctylmaleate supply. In this case, the solubility limit can be a dioctyltin bisoctylmaleate supply having less than 12, 11.5, 11, 10.5, 10, 9.5, 9, 8.5 or 8 weight percent dioctyltin maleate based on the total weight of the dioctyltin bisoctylmaleate sample tested to detect the presence of dioctyltin maleate.

In another example, the solubility limit, as a reference value, can be characterized as a calculated ratio of relative intensities or peak intensities of dioctyltin bisoctylmaleate and dioctyltin maleate. For instance, the presence of dioctyltin bisoctylmaleate and dioctyltin maleate in a test sample can appear as individual peaks on a HPLC chromatograph. The individual peaks of these components have a maximum value or relative intensity. Examples of such chromatographs and relative intensities are shown in FIGS. 2 through 7. The ratio of the relative intensities of these components can be used to determine the quality of the dioctyltin bisoctylmaleate supply in terms of its concentration of dioctyltin maleate. Thus, the solubility limit can be characterized as a dioctyltin bisoctylmaleate supply having a ratio of the relative intensity of dioctyltin bisoctylmaleate to the relative intensity of dioctyltin maleate in the range of 1.8 to 3.2 or more than 1.8, 1.9, 2, 2.1, 2.2, 2.4, 2.6, 2.8 or 3. Alternatively, the solubility limit can be characterized as a dioctyltin bisoctylmaleate supply having a ratio of the relative intensity of dioctyltin maleate to the relative intensity of dioctyltin bisoctylmaleate in the range of 0.3 to 0.54 or less than 0.53, 0.52, 0.51, 0.5, 0.48, 0.45, 0.4, 0.35 or 0.32.

The measured solubility limit of a sample can be compared to a baseline value and also be used to make qualitative decisions, for example, it can be used to prompt a yes or no decision about the dioctyltin bisoctylmaleate supply or material. For instance, the quality of a dioctyltin bisoctylmaleate supply can be evaluated by analyzing a sample to determine the presence of dioctyltin maleate or its weight percent or relative intensity by HPLC or other methods. The measured data can be compared to a solubility limit reference value to determine whether the dioctyltin bisoctylmaleate supply is above or below the solubility limit threshold for use of it in a polymer process. An example of a decision is whether to accept the dioctyltin bisoctylmaleate supply if the analysis of the sample is below the acceptable solubility limit or, alternatively, a decision to reject the use of the dioctyltin bisoctylmaleate supply can be made if the analysis shows that it is above the acceptable solubility limit.

The qualitative decisions based on the evaluation of a dioctyltin bisoctylmaleate supply are of interest in processes for preparing polymers that utilize the dioctyltin bisoctylmaleate supplies. Being able to evaluate the quality of a dioctyltin bisoctylmaleate supply and make decisions prior to using the dioctyltin bisoctylmaleate supply in a process for preparing a polymer can eliminate or reduce manufacturing problems associated with impurities present in the dioctyltin bisoctylmaleate supply, such as precipitates. Likewise, the methods described herein can include the polymers made by processes that implement the quality control methods and steps of sampling and analyzing dioctyltin bisoctylmaleate supplies prior to use and thereby making decisions based on solubility limits and data generated by testing and evaluating the samples.

The methods described herein also can include providing a record, such as a certificate of analysis (COA) regarding dioctyltin maleate content or dioctyltin bisoctylmaleate quality, or alternative print or computer readable records, for a dioctyltin bisoctylmaleate supply for use in a polymer process. The print materials or records can include additional information, such as HPLC method details, a test date, an operator of the method, or information about the dioctyltin bisoctylmaleate source, etc. The COA, print or record can be used to make a decision whether to accept, use, discard, reject or withhold the dioctyltin bisoctylmaleate supply from a polymer process. In another embodiment, the methods can include memorializing or further recording the decision or step taken based on the COA, print or record. In another embodiment, the COA, print or record can be included with the polymer product made by the process that implemented the quality control and evaluation methods described herein.

The methods of evaluating the quality of dioctyltin bisoctylmaleate can include obtaining information regarding its dioctyltin maleate content and evaluating whether that content is above or below a reference solubility limit, wherein the information can be obtained by the methods herein. A decision can be made upon receipt of the information, for example, transmitting the information to a party which makes a decision, e.g., to classify, accept or discard, release or withhold, process into a polymer product, move to a different location, or process for further purification, e.g., remove precipitate, at least in part, upon the information or analysis of the data or chromatographs generated by the methods herein.

The methods described herein also allow for dioctyltin maleate and other impurities to be resolved from other components in the dioctyltin bisoctylmaleate supply, such as dioctyltin bisoctylmaleate itself. The term "resolve," "resolved," or "resolving" means to determine that two components are distinct from one another. For example, the HPLC methods described herein can result in chromatographs that distinguish dioctyltin maleate from dioctyltin bisoctylmaleate such that each component can be analyzed individually in terms of weight percent, peak shape and relative intensity.

In one embodiment, a method of choice is the use of HPLC coupled with a detector. HPLC is a chromatographic separation technique in which high-pressure pumps force the substance or mixture being analyzed together with the mobile phase, also referred to as the eluent, through a separating column containing a stationary phase. The dioctyltin bisoctylmaleate and the impurities present, if any, are separated on the HPLC stationary phase and they can be detected and quantified using their response once they leave the column in the mobile phase.

HPLC operation can be performed in a gradient mode. A gradient HPLC mode is carried by a gradual change over a period of time in the percentage of the two or more solvents in the mobile phase. The change in solvent is controlled by a mixer which mixes the solvents to produce a mobile phase prior to its passing through the column. If a substance interacts strongly with the stationary phase, it remains in the column for a relatively long time, whereas a substance that does not interact as strongly with the stationary phase elutes out of the column sooner.

Similarly, the selection of solvents can affect the effectiveness of the separation. For instance, a strong and weak solvent can be selected for the components to be separated and varying the gradient, i.e. the concentration of each solvent over time, can force separation and aid interaction of one or more components with the stationary phase. Depending on the strength of interactions, such as with the stationary phase and solvents, components preferably appear at the end of the column at distinct and different times, also referred to as retention times. As shown in the Examples, the methods described herein provide fast, efficient and reliable ways to accurately access the individual components present in dioctyltin bisoctylmaleate supplies.

HPLC analysis of a sample begins with preparing a HPLC test sample from the dioctyltin bisoctylmaleate supply. The HPLC test sample can have a sample of a dioctyltin bisoctylmaleate supply present in a concentration in the range of 0.1 to 2 weight percent, or between 0.1 and 1 weight percent, or between 0.1 and 0.5 weight percent or 0.2, 0.3 or 0.4 weight percent. A sample of the dioctyltin bisoctylmaleate supply can be mixed into solution with two or more solvents, for instance, a first solvent and a second solvent. Optionally, a third and fourth solvent can be used to prepare the HPLC test sample. To detect and measure the presence of dioctyltin bisoctylmaleate and other impurities, such as dioctyltin maleate, the solvents are selected such that dioctyltin bisoctylmaleate and dioctyltin maleate are soluble in one or more of the solvents. The solvents are preferably non-aqueous. The solvents can be organic solvents, for example, the solvents can be selected from chlorinated solvents or chloromethanes, such as chloroform and methylene chloride, and cycloalkanes, such as cyclohexane, or tetrahydrofuran (THF). Other suitable solvents can be used depending on the particular impurities being analyzed. The referenced solvents or combinations of solvents noted above for preparing the HPLC test sample can also be used for the HPLC mobile phase.

The two or more solvents can be mixed in a desirable ratio to ensure that dioctyltin bisoctylmaleate and diocytltin maleate or other impurities are dissolved for loading onto the column. For example, in a two-solvent or co-solvent system, the first and second solvents can be present at a ratio of 10:90 to 90:10 or 20:80 to 80:20 or 30:70 or 70:30 or 40:60 or 60:40 or 50:50.

The HPLC test sample can be loaded onto the column at an amount or injection volume in the range of 5 to 100 µl, or preferably 5 to 25 µl or 10 µl. The mobile phase flow rate can be between 0.1 to 2 ml/min, or 0.25, 0.5, 0.75, 1, 1.25, 1.5 or 1.75 ml/min. The mobile phase of the column can include two or more liquids and can be the same or similar to the solvents, e.g., the first solvent and the second solvent, referenced above for preparing the HPLC test sample. Ternary and quaternary systems including a respective third and fourth solvent optionally can be used for the mobile phase. Such third and fourth solvents can be selected from those noted above for the HPLC test sample.

With regard to the stationary phase, substrates, such as resin or beads, suitable for HPLC can be silica or coated with materials, such as a $C_{18}$ material, for example, with iso-butyl side chains and with TMS endcapping, e.g., Kinetex® XB-C18, or a phenyl hexyl material. Preferably, the stationary phase is polar to support normal phase HPLC. The stationary phase can have a particle size of between 0.1 and 10 µm, or between 1 and 5 µm or between 2 and 4 or 2.6 µm. The stationary phase can have a pore size of between 10 and 500 Å, or between 50 and 250 Å or 100, 150 or 200 Å.

In one embodiment, the chromatography can be carried out in a column between 10 and 250 mm in length, or in a column between 50 and 200 mm in length, or between 75 and 150 mm in length, and preferably in a column 100 or 125 mm in length. The chromatography can be carried out in a column having an internal diameter in the range of 0.1 to 10 mm, or between 1 and 5 mm or 2, 3, 3.5, 4 or 4.6 mm. In another embodiment, longer and wider columns as compared to those noted above can be used for the chromatography.

The column can be maintained at a constant temperature throughout the separation of components, e.g., using a commercial column heater. In some embodiments, the column can be maintained at a temperature in the range of 10° to 40° C., or at 15, 20, 25, 30 or 35° C. The single run time of the HPLC can be in the range of 10 to 30 minutes or less than 25, 20, 15, 12 or 10 minutes.

Dioctyltin bisoctylmaleate, dioctyltin maleate and other impurities exiting the column in the eluent, preferably at different retention times, can be detected by numerous methods and equipment, for example, by ultraviolet absorbance, a visible spectrophotometer, a fluorescence spectrophotometer, a differential refractometer, an electrochemical detector, a mass spectrometer, or with an evaporative light scattering detector. In one embodiment, as used in the Examples below, the detector preferably is evaporative light scattering detector.

In one embodiment, the HPLC method can be programmed such that the relative concentrations of the liquids, e.g., solvents, of the mobile phase are varied to a predetermined gradient. The predetermined gradient is preferably used for analyzing the quality of dioctyltin bisoctylmaleate materials. The predetermined gradient can be used to detect dioctyltin bisoctylmaleate and its impurities and is preferably selected that such components are separated and can be analyzed individually. In an embodiment, the HPLC method detects and optionally quantifies in a single run one or more of the following: 1) dioctyltin bisoctylmaleate; 2) dioctyltin maleate and 3) other unknown impurities.

An example pump gradient can vary the relative concentrations by volume of a first and second solvent, respectively A and B. Starting relative concentrations can be 60 to 90% A or preferably 80% A and 10 to 40% B or preferably 20% B. The starting relative concentrations can be varied to separate one or more components on the stationary phase. To achieve such separation, the relative concentration of A can be varied to be 10 to 30% or 20% and the relative concentration of B can be varied to be 70 to 90% or 80%. Subsequently, the gradient can be returned to the starting concentrations of A and B to begin another run. Solvents A and B can be the same or similar to the solvents referenced above for preparing the HPLC test sample.

In another example, A can be cyclohexane and B can be chloroform and the gradient can be as shown below in Example 1.

In another embodiment, the dioctyltin bisoctylmaleate and dioctyltin maleate compounds can be used as internal reference standards or markers. In another embodiment, the HPLC method is suitable for use in the analysis of dioctyltin bisoctylmaleate intended for use in a process to prepare a polymer. Preferably, the HPLC method is used for analysis of dioctyltin bisoctylmaleate prior to its use in a polymer process. Alternatively, the HPLC method can be used to analyze dioctyltin bisoctylmaleate materials after a portion of the materials have been utilized in a polymer process. In this later case, the HPLC method can be used to troubleshoot problems during polymer manufacturing or analyze polymer quality.

Figure 5:
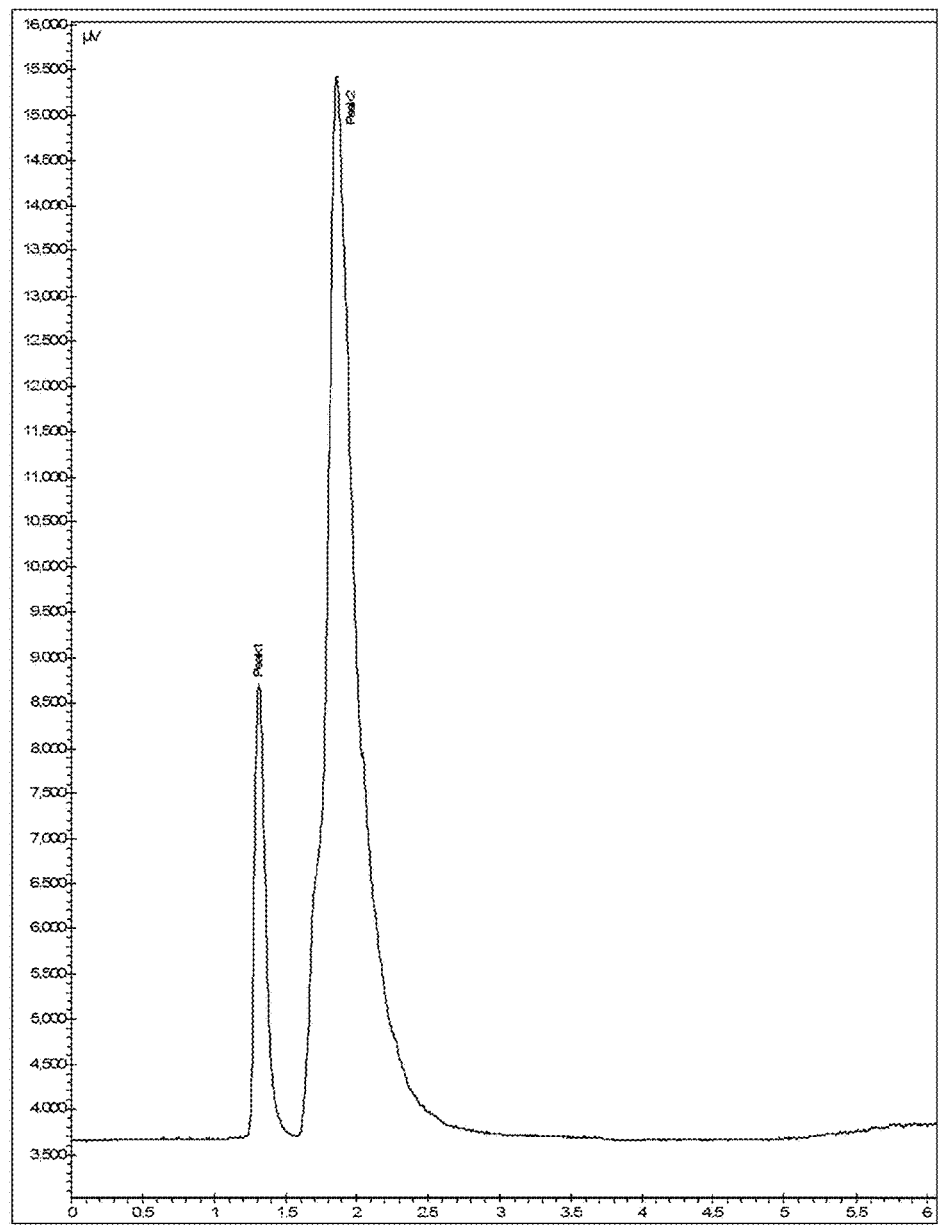
FIG. 5 is a HPLC chromatograph of a sample from a dioctyltin bisoctylmaleate supply showing the presence of dioctyltin maleate and other impurities.
Figure 6:
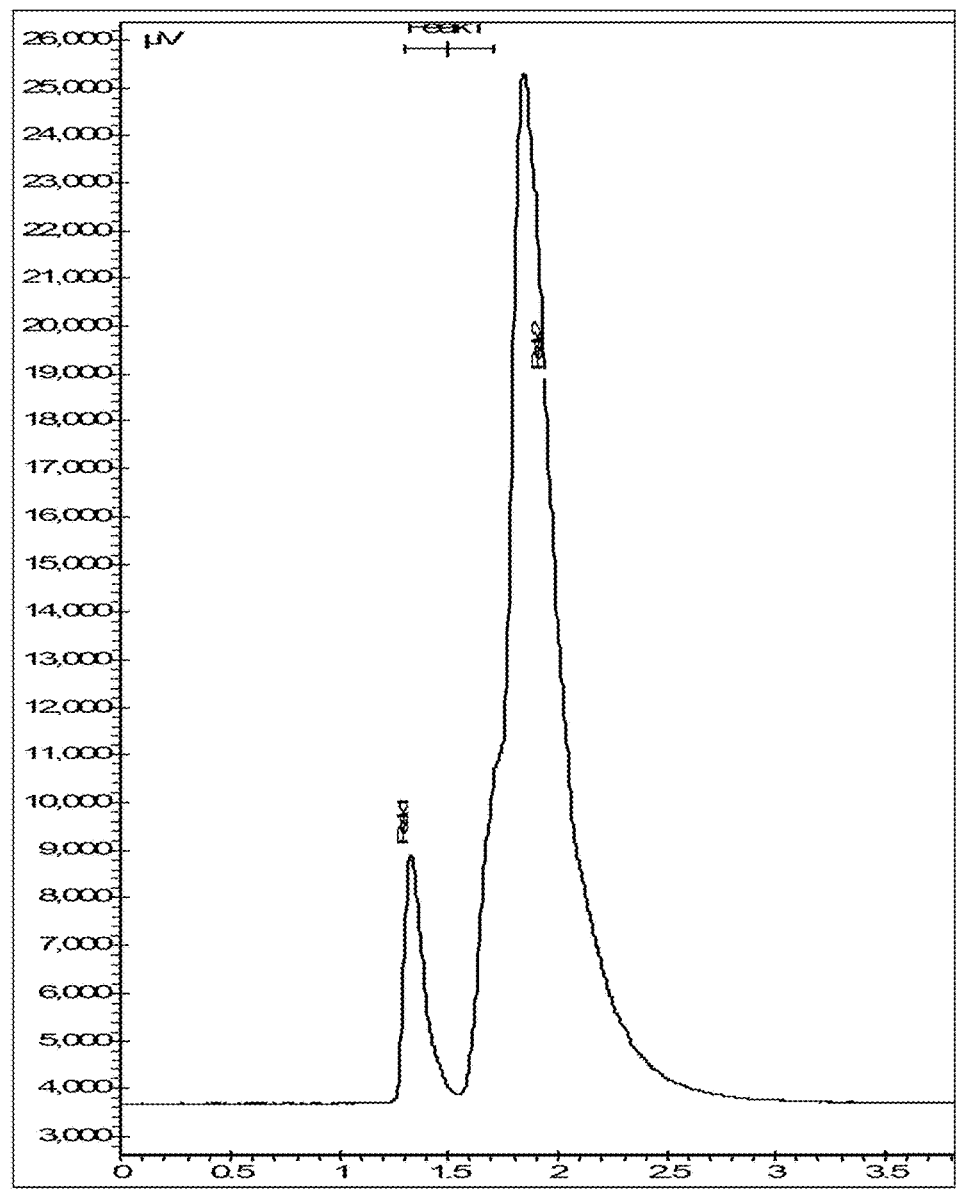
FIG. 6 is a HPLC chromatograph of a sample from a dioctyltin bisoctylmaleate supply showing the presence of dioctyltin maleate and other impurities.

Turning to the Figures, it is shown that dioctyltin bisoctylmaleate supplies can have additional impurities other than diocytltin maleate. For example, FIGS. 5 and 6 show dioctyltin bisoctylmaleate being present at a retention time of 1.9 minutes. Those Figures further show that the peaks for dioctyltin bisoctylmaleate have a shoulder or bump along the leading edge or first half of the peak, i.e., the beginning of the peak to the maximum intensity point at the top of the peak. In contrast, FIG. 7 does not show such a shoulder on the leading edge of the peak for dioctyltin bisoctylmaleate. The impurity or impurities responsible for the presence of the shoulder are unknown, however, such components may have a negative impact on a polymer process, such as forming by products by reacting with components in the process or being present in the final polymer product.

Dioctyltin bisoctylmaleate material can be evaluated to detect the presence of the one or more impurities that cause the presence of the shoulder. A decision can be made based on the detection of the presence of the shoulder as described above except that the solubility limit is not the factor that forms the basis for the decision. For example, detection of the shoulder can be made visually by observation of a chromatograph, such as those shown in FIGS. 5 and 6. Detection of the shoulder can also be made by a mathematical analysis of the dioctyltin bisoctylmaleate peak in the chromatograph.

Figure 7:
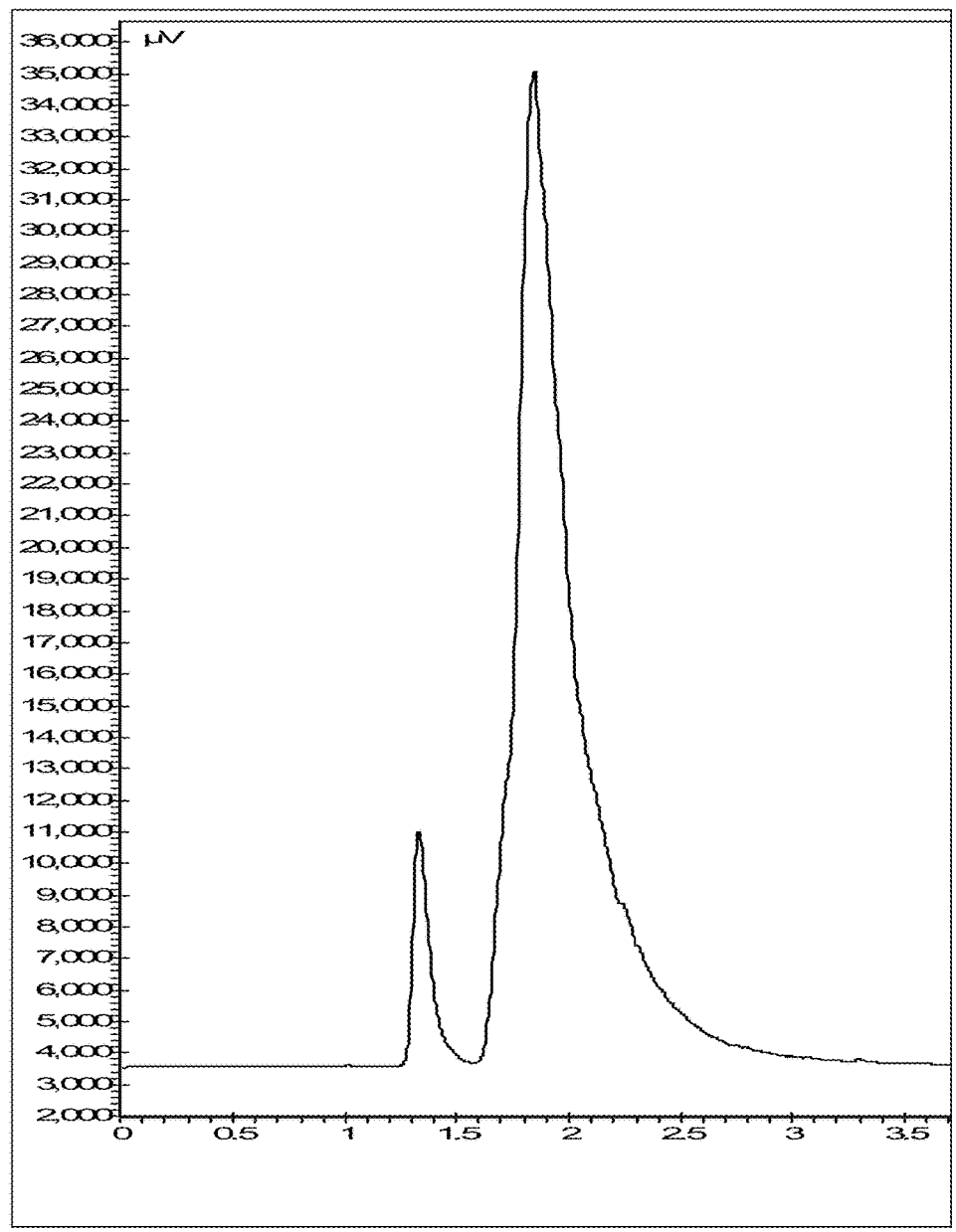
FIG. 7 is a HPLC chromatograph of a sample from a dioctyltin bisoctylmaleate supply showing the presence of dioctyltin maleate.

The leading edge of the peak has a continually increasing (i.e. in slope) tangent line along its face starting from the beginning of the peak to near the top of the peak at the maximum value or at least 0.01 to 0.05 minutes before the retention time at the peak maximum, or about 1.9 minutes. Such a continuous increase in the progressive tangent line indicates that the one or more impurities causing the shoulder are not present in a detectable amount in the dioctyltin bisoctylmaleate sample. In contrast, if the one or more impurities are present in a detectable amount, the progressive tangent line is not continually increasing from the beginning of the peak to near the top. Rather, the first half of the dioctyltin bisoctylmaleate peak will have a period where the progressive tangent line decreases in angle or slope as the tangent line progresses along the front half of the peak curve and reaches the shoulder region. For example, the shoulder creates a curvature that follows a path towards the center of the peak rather than steadily increasing towards the top of the peak as shown in FIG. 7. The change in curvature of the shoulder causes the progressing tangent line along the front half of the peak to also change in angle in a decreasing manner and point back towards the center of the peak before it subsequently increases again once it is past the shoulder area.

As described above, the presence of the shoulder in the dioctyltin bisoctylmaleate peak can be used to make qualitative decisions, for example, it can be used to trigger a yes or no decision about the dioctyltin bisoctylmaleate supply or material. The detected shoulder presence can be used to decide whether the dioctyltin bisoctylmaleate supply should be accepted or rejected for use in a polymer process.

Such decisions are of interest in processes to prepare polymers that can utilize dioctyltin bisoctylmaleate supplies.

Being able to evaluate the quality of a dioctyltin bisoctylmaleate supply and make decisions prior to using the dioctyltin bisoctylmaleate supply in a process for preparing a polymer can eliminate manufacturing problems associated with impurities present in the dioctyltin bisoctylmaleate supply. Likewise, the methods described herein can relate to the polymers made by processes that implement the quality control steps of sampling and analyzing dioctyltin bisoctylmaleate supplies prior to use and thereby making decisions based on shoulder presence and data generated by testing the samples.

In order to demonstrate the practice of the present invention, the following examples have been prepared and tested. The examples should not, however, be viewed as limiting the scope of the invention.

EXAMPLE 1

Dioctyltin bisoctylmaleate material was evaluated by HPLC. The dioctyltin bisoctylmaleate material did not contain visual precipitate at 25° C. prior to testing. The HPLC conditions were a mobile phase flow of 1 ml/min and the column was maintained at 35° C. The column was made by Phenomenex, model Kinitex®, 2.6 µm XB-C18 100 Å with an evaporative light scattering detector (ELSD). Column dimensions were 150 mm×4.6 mm. HPLC test samples were prepared by dissolving a portion of the dioctyltin bisoctylmaleate material at a concentration of 0.3% (w/w) in a 50:50 mixture of chloroform and cyclohexane. The injection volume of the HPLC test sample was 10 µl.

The HPLC column mobile phase included two solvents: (A) cyclohexane and (B) chloroform. The pump gradient used to process the HPLC test sample is shown below in Table 1 and FIG. 1. The total run time was 15 minutes.

TABLE 1

| Time (min) | Flow (ml/min) | % Cyclohexane | % Chloroform |
|---|---|---|---|
| 0 | 1 | 80 | 20 |
| 2 | 1 | 80 | 20 |
| 8 | 1 | 10 | 90 |
| 9 | 1 | 80 | 20 |
| 15 | 1 | 80 | 20 |

As can be seen from the pump gradient, the column begins operation for the first 2 minutes with a 80:20 mixture of cyclohexane:chloroform. After 2 minutes, the amount of chloroform was linearly reduced up to 8 minutes to reach a 10:90 mixture of cyclohexane:chloroform. The mixture was quickly brought back to a 80:20 mixture of cyclohexane: chloroform by 9 minutes and was allowed to remain constant at that concentration for the remainder of the run time.

Figure 2:
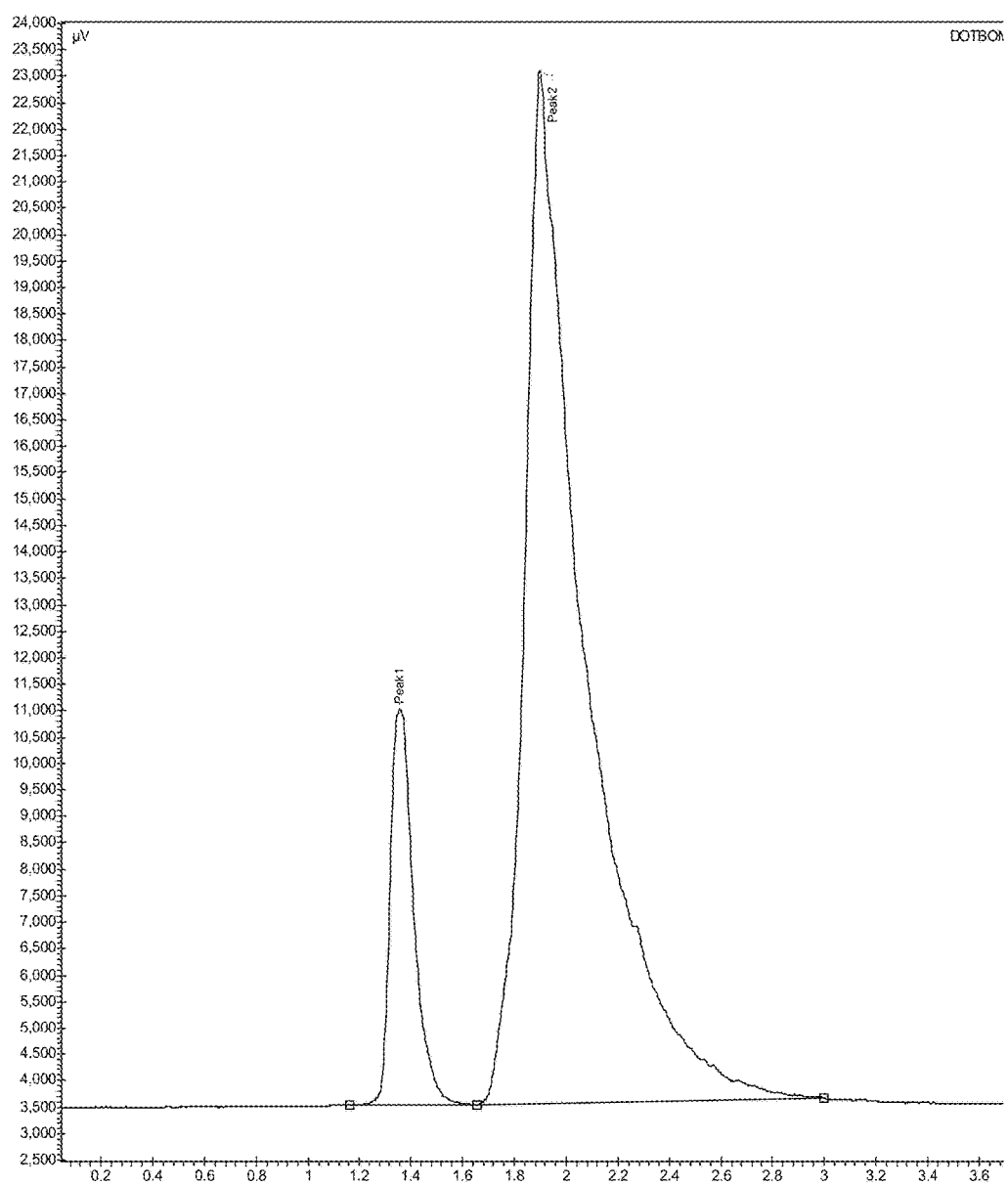
FIG. 2 is a HPLC chromatograph of a sample from a dioctyltin bisoctylmaleate supply showing the presence of dioctyltin maleate.

FIG. 2 shows a chromatograph from the HPLC analysis of the test sample. The HPLC analysis detected that the test sample contained 10.6 weight percent of dioctyltin maleate and 89.4 weight percent of dioctyltin bisoctylmaleate. The first peak, having a maximum intensity at 1.3 minutes of 11,000 µV, represents the dioctyltin maleate present in the dioctyltin bisoctylmaleate sample. The second peak, having a maximum intensity at 1.9 minutes of 23,100 represents dioctyltin bisoctylmaleate. The ratios of relative intensities of dioctyltin maleate to dioctyltin bisoctylmaleate, and vice versa, are shown as 2.1 and 0.48, respectively. The solubility limit of dioctyltin maleate is at least 10.6 weight percent at 25° C. and at a ratio of greater than 2 or less than 0.48.

EXAMPLE 2

Figure 3:
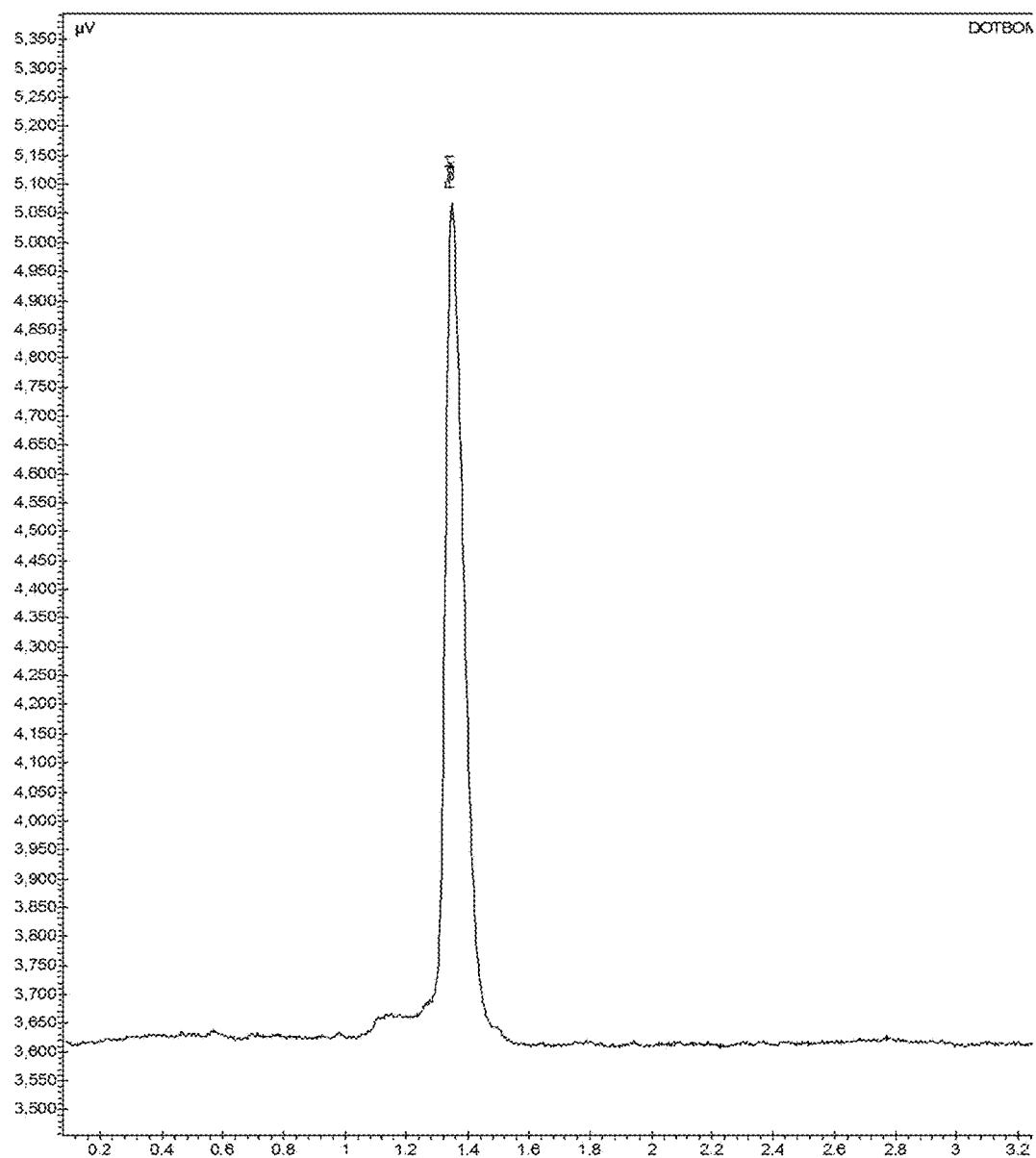
FIG. 3 is a HPLC chromatograph of a sample from a dioctyltin bisoctylmaleate supply showing the presence of dioctyltin maleate.

Dioctyltin bisoctylmaleate material was evaluated by HPLC. The dioctyltin bisoctylmaleate material did contain visual precipitate at 25° C. prior to testing. The precipitate was determined to be dioctyltin maleate. To analyze the precipitate, it was separated from the dioctyltin bisoctylmaleate material and cleaned with several hexane washes followed by centrifugation and drying in a vacuum oven without heat overnight before HPLC analysis. A HPLC test sample of the dried material was prepared at a concentration of 0.3% (w/w) in a 50:50 mixture of chloroform and cyclohexane. The same column and conditions as in Example 1 were used to evaluate the HPLC test sample. FIG. 3 shows a chromatograph from the HPLC analysis of the test sample.

The HPLC analysis confirmed that the precipitate was dioctyltin maleate. As shown, there is a single peak at about 1.3 minutes, which suggests that only dioctyltin maleate was precipitating from the dioctyltin bisoctylmaleate material.

Figure 4:
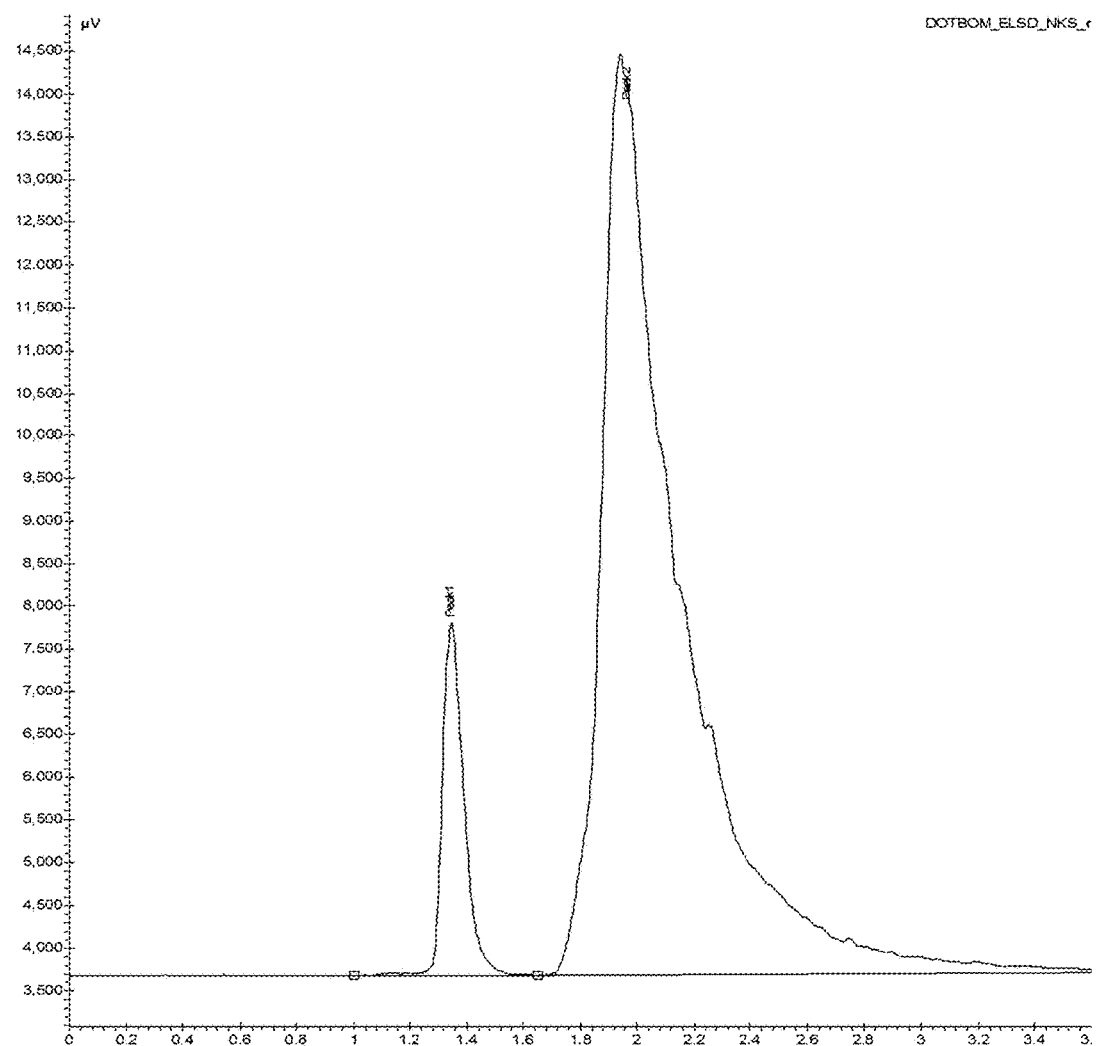
FIG. 4 is a HPLC chromatograph of a sample from a dioctyltin bisoctylmaleate supply showing the presence of dioctyltin maleate.

To analyze the liquid portion of the dioctyltin bisoctylmaleate material, separate from the precipitate, liquid material from the top of the dioctyltin bisoctylmaleate material was carefully pipetted off for the liquid portion analysis. The removed liquid material was visually inspected to ensure no precipitate was present. A HPLC test sample of the liquid material was prepared at a concentration of 0.3% (w/w) in a 50:50 mixture of chloroform and cyclohexane. The same column and conditions as in Example 1 were used to evaluate the HPLC test sample. FIG. 4 shows a chromatograph from the HPLC analysis of the test sample.

The HPLC analysis detected that the test liquid only sample contained 9.4 weight percent of dioctyltin maleate and 90.6 weight percent of dioctyltin bisoctylmaleate. The first peak, having a maximum intensity at 1.3 minutes of 7,800 µV, represents the dioctyltin maleate present in the dioctyltin bisoctylmaleate sample. The second peak, having a maximum intensity at 1.9 minutes of 14,500 µV, represents dioctyltin bisoctylmaleate. The ratios of relative intensities of dioctyltin maleate to dioctyltin bisoctylmaleate, and vice versa, are shown as 1.86 and 0.54, respectively. The solubility limit of dioctyltin maleate is at least 9.4 weight percent at 25° C. and at a ratio of greater than 1.8 or less than 0.54.

EXAMPLE 3 dioctyltin bisoctylmaleate material was evaluated by HPLC. The dioctyltin bisoctylmaleate material did contain visual precipitate at 25° C. prior to testing. The precipitate was determined to be dioctyltin maleate.

A HPLC test sample of the material was prepared at a concentration of 0.3% (w/w) in a 50:50 mixture of chloroform and cyclohexane. To form the HPLC sample, the dioctyltin bisoctylmaleate material was stirred continuously for 5 minutes to create a homogenous mixture of liquid and precipitate. The 0.05 g of the liquid precipitate mixture was dissolved in 16 g of 50:50 chloroform:cyclohexane and filtered through a 0.45 micron syringe filter prior to being added to the column. The same column and conditions as in Example 1 were used to evaluate the HPLC test sample. FIG. 5 shows a chromatograph from the HPLC analysis of the test sample.

The HPLC analysis detected that the test sample contained 12.5 weight percent of dioctyltin maleate and 87.5 weight percent of dioctyltin bisoctylmaleate. The first peak, having a maximum intensity at 1.3 minutes of 8,500 µV, represents the dioctyltin maleate present in the dioctyltin bisoctylmaleate sample. The second peak, having a maximum intensity at 1.9 minutes of 15,200 µV, represents dioctyltin bisoctylmaleate. The ratios of relative intensities of dioctyltin maleate to dioctyltin bisoctylmaleate, and vice versa, are shown as 1.8 and 0.56, respectively. Based on the visible presence of dioctyltin maleate precipitate in the dioctyltin bisoctylmaleate material, the solubility limit of dioctyltin maleate is below 12.5 weight percent at 25° C. The solubility limit is also at a ratio of greater than 1.8, and from Example 2 above, less than 0.54.

EXAMPLE 4 dioctyltin bisoctylmaleate material was evaluated by HPLC. The dioctyltin bisoctylmaleate material did contain visual precipitate at 25° C. prior to testing. The precipitate was determined to be dioctyltin maleate.

A HPLC test sample of the material was prepared at a concentration of 0.3% (w/w) in a 50:50 mixture of chloroform and cyclohexane. To form the sample, clear liquid was drawn off the top of the material. The sample liquid did not contain any visual precipitate. The same column and conditions as in Example 1 were used to evaluate the HPLC test sample. FIG. 6 shows a chromatograph from the HPLC analysis of the test sample.

The HPLC analysis detected that the test liquid only sample contained 8.3 weight percent of dioctyltin maleate and 91.5 weight percent of dioctyltin bisoctylmaleate. The first peak, having a maximum intensity at 1.3 minutes of 8,750 µV, represents the dioctyltin maleate present in the dioctyltin bisoctylmaleate sample. The second peak, having a maximum intensity at 1.9 minutes of 25,250 µV, represents dioctyltin bisoctylmaleate. The ratios of relative intensities of dioctyltin maleate to dioctyltin bisoctylmaleate, and vice versa, are shown as 2.9 and 0.35, respectively. The solubility limit of dioctyltin maleate is at least 8.3 weight percent at 25° C. and at a ratio of less than 2.9 or more than 0.35.

EXAMPLE 5 dioctyltin bisoctylmaleate material was evaluated by HPLC. The dioctyltin bisoctylmaleate material did not have any visual precipitate.

A HPLC test sample of the material was prepared at a concentration of 0.3% (w/w) in a 50:50 mixture of chloroform and cyclohexane. The same column and conditions as in Example 1 were used to evaluate the HPLC test sample. FIG. 7 shows a chromatograph from the HPLC analysis of the test sample.

The HPLC analysis detected that the test liquid only sample contained 8.5 weight percent of dioctyltin maleate and 91.5 weight percent of dioctyltin bisoctylmaleate. The first peak, having a maximum intensity at 1.3 minutes of 11,500 µV, represents the dioctyltin maleate present in the dioctyltin bisoctylmaleate sample. The second peak, having a maximum intensity at 1.9 minutes of 34,500 µV, represents dioctyltin bisoctylmaleate. The ratios of relative intensities of dioctyltin maleate to dioctyltin bisoctylmaleate, and vice versa, are shown as 3 and 0.33, respectively. The solubility limit of dioctyltin maleate is at least 8.5 weight percent at 25° C. and at a ratio of less than 3 or more than 0.33.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting.

The invention claimed is:

1. A process for preparing a polymer, comprising:
    sampling a dioctyltin bis(octylmaleate) supply to generate a dioctyltin bis(octylmaleate) sample comprising dioctyltin bis(octylmaleate) and dioctyltin maleate; measuring the dioctyltin bis(octylmaleate) sample to determine at least one of the following:
    a ratio of peak intensities of a peak intensity of the dioctyltin bis(octylmaleate) and a peak intensity of the dioctyltin maleate in the dioctyltin bis(octylmaleate) sample, the peak intensities being measured by HPLC; or
    weight percent of the dioctyltin maleate present in the dioctyltin bis(octylmaleate) sample;
    selecting the dioctyltin bis(octylmaleate) supply for use as a reagent to prepare a polymer, wherein the dioctyltin bis(octylmaleate) sample from the dioctyltin bis(octylmaleate) supply contains less than 12 weight percent of the dioctyltin maleate or a ratio of the peak intensity of the dioctyltin bis(octylmaleate) to the peak intensity of the dioctyltin maleate in the dioctyltin bis(octylmaleate) is above 1.8; and
    using the dioctyltin bis(octylmaleate) supply to prepare a polymer based upon the measuring of the dioctyltin bis (octylmaleate) sample.

2. The process for preparing a polymer of claim 1, further comprising using the dioctyltin bis(octylmaleate) sample to prepare a HPLC test sample for use in measuring the ratio of the peak intensities of the peak intensity of the dioctyltin bis(octylmaleate) and the peak intensity of the dioctyltin maleate in the dioctyltin bis(octylmaleate) sample.

3. The process for preparing a polymer of claim 2, the HPLC test sample comprising a first solvent and a second solvent.

4. The process for preparing a polymer of claim 3, the dioctyltin maleate in the dioctyltin bis(octylmaleate) sample being soluble in the first solvent.

5. The process for preparing a polymer of claim 3, the dioctyltin maleate in the dioctyltin bis(octylmaleate) sample being soluble in the second solvent.

6. The process for preparing a polymer of claim 1, wherein the ratio of the peak intensity of the dioctyltin bis(octylmaleate) to the peak intensity of the dioctyltin maleate is above 2.

7. The process for preparing a polymer of claim 1, wherein a ratio of the peak intensity of the dioctyltin maleate to the peak intensity of the dioctyltin bis(octylmaleate) is below 0.54.

8. The process for preparing a polymer of claim 1, wherein the dioctyltin maleate in the dioctyltin bis(octylmaleate) sample is less than 10 weight percent.

9. The process for preparing a polymer of claim 1, wherein the dioctyltin maleate in the dioctyltin bis(octylmaleate) sample is less than 11 weight percent.

10. A process for preparing a polymer, comprising:
    preparing a HPLC test sample with a dioctyltin bis(octylmaleate) material and two or more liquids, wherein the dioctyltin bis(octylmaleate) material contains dioctyltin bis(octylmaleate) and dioctyltin maleate and the dioctyltin maleate is soluble in at least one of the two or more liquids of the HPLC test sample, and wherein the dioctyltin bis(octylmaleate) material is sampled from a dioctyltin bis(octylmaleate) supply;
    measuring the dioctyltin bis(octylmaleate) material of the HPLC test sample by HPLC to determine at least one of the following:

the weight percent of dioctyltin maleate present in the dioctyltin bis(octylmaleate) material; or a ratio of peak intensities of a peak intensity of the dioctyltin maleate and a peak intensity of the dioctyltin bis(octylmaleate) in the dioctyltin bis(octylmaleate) material;

selecting the dioctyltin bis(octylmaleate) supply for use as a reagent to prepare a polymer, wherein the dioctyltin bis(octylmaleate) material from the the dioctyltin bis(octylmaleate) supply contains less than 12 weight percent of dioctyltin maleate or a ratio of the peak intensity of the dioctyltin bis(octylmaleate) to the peak intensity of the dioctyltin maleate in the dioctyltin bis(octylmaleate) material is above 1.8; and using the dioctyltin bis(octylmaleate) supply to prepare a polymer based upon the measuring of the dioctyltin bis(octylmaleate) material.

11. The process of claim 10, the two or more liquids being a first solvent and a second solvent.

12. The process of claim 11, the relative concentrations of the first solvent and the second solvent being varied to a predetermined gradient, wherein the first and second solvents are selected from chloroform and cyclohexane.

13. The process of claim 10, wherein the ratio of the peak intensity of the dioctyltin bis(octylmaleate) to the peak intensity of the dioctyltin maleate is above 2.

14. The process of claim 10, wherein a ratio of the peak intensity of the dioctyltin maleate to the peak intensity of the dioctyltin bis(octylmaleate) is below 0.54.

15. The process of claim 10, wherein the dioctyltin bis(octylmaleate) material from the dioctyltin bis(octylmaleate) supply contains less than 11 weight percent of dioctyltin maleate.

16. The process of claim 10, wherein the dioctyltin bis(octylmaleate) material from the dioctyltin bis(octylmaleate) supply contains less than 10 weight percent of dioctyltin maleate.

* * * * *